United States Patent
Mangual-Soto et al.

(10) Patent No.: US 11,235,158 B2
(45) Date of Patent: Feb. 1, 2022

(54) METHOD AND SYSTEM FOR BIVENTRICULAR OR LEFT VENTRICULAR PACING

(71) Applicant: PACESETTER, INC., Sylmar, CA (US)

(72) Inventors: Jan O. Mangual-Soto, Rho (IT); Nima Badie, Berkeley, CA (US); Luke C. McSpadden, Los Angeles, CA (US); Jong Gill, Valencia, CA (US); Louis-Philippe Richer, Montreal (CA)

(73) Assignee: PACESETTER, INC., Sylmar, CA (US)

( * ) Notice: Subject to any disclaimer, the term of this patent is extended or adjusted under 35 U.S.C. 154(b) by 254 days.

(21) Appl. No.: 16/128,246

(22) Filed: Sep. 11, 2018

(65) Prior Publication Data
US 2020/0078591 A1    Mar. 12, 2020

(51) Int. Cl.
*A61N 1/36* (2006.01)
*A61N 1/368* (2006.01)
*A61N 1/365* (2006.01)
*A61N 1/02* (2006.01)

(52) U.S. Cl.
CPC ......... *A61N 1/3682* (2013.01); *A61N 1/025* (2013.01); *A61N 1/3684* (2013.01); *A61N 1/3686* (2013.01); *A61N 1/3688* (2013.01); *A61N 1/36592* (2013.01)

(58) Field of Classification Search
CPC ... A61N 1/3627; A61N 1/3682; A61N 1/3684
See application file for complete search history.

(56) References Cited

U.S. PATENT DOCUMENTS

| | | | |
|---|---|---|---|
| 2003/0130702 A1* | 7/2003 | Kramer | A61N 1/3956 607/9 |
| 2004/0158293 A1* | 8/2004 | Yonce | A61N 1/3712 607/9 |

(Continued)

OTHER PUBLICATIONS

Ducharme et al., "Left Ventricular Versus Simultaneous Biventricular Pacing in Patients With Heart Failure and a QRS Complex ≥120 Milliseconds", Circulation 2011; 124: 2874-81; 13 pages.

*Primary Examiner* — Michael J D'Abreu
(74) *Attorney, Agent, or Firm* — The Small Patent Law Group LLC; Dean D. Small

(57) ABSTRACT

Systems and methods are provided for detecting arrhythmias in cardiac activity is provided. The systems and methods include measuring conduction delays between an atria (A) and multiple left ventricular (LV) electrodes to obtain multiple intrinsic A/LV intervals, measuring conduction delays between a right ventricular (RV) and the multiple LV electrodes to obtain multiple intrinsic VV intervals. The systems and methods include calculating a first atrial ventricular (AV) delay based on at least one of the intrinsic A/LV intervals, and calculating a second AV delay based on at least one of the intrinsic VV intervals. The systems and methods include selecting a biventricular (BiV) pacing mode or an LV only pacing mode based on a relation between the first and second AV delays, and delivering a pacing therapy based on the selecting operation.

20 Claims, 4 Drawing Sheets

(56) References Cited

U.S. PATENT DOCUMENTS

| | | | | |
|---|---|---|---|---|
| 2005/0027323 A1* | 2/2005 | Mulligan | ............. | A61N 1/3627 607/18 |
| 2010/0087889 A1* | 4/2010 | Maskara | ............ | A61N 1/36843 607/25 |
| 2011/0022112 A1* | 1/2011 | Min | ................... | A61N 1/36842 607/25 |
| 2017/0340887 A1* | 11/2017 | Engels | ................. | A61B 5/0468 |

* cited by examiner

METHOD AND SYSTEM FOR BIVENTRICULAR OR LEFT VENTRICULAR PACING

FIELD OF THE INVENTION

Embodiments herein generally relate to implantable medical devices, and more particularly to determining to implement biventricular (BiV Pacing) or left ventricular (LV Pacing).

BACKGROUND OF THE INVENTION

Advances in implantable medical devices (IMD) and left ventricular (LV) lead design has improved electrical stimulation, delays, and pacing, resulting in a better patient outcome. Loss of atrioventricular (AV) electrical and mechanical synchrony can result in inadequate ventricular depolarization, leading to suboptimal therapy. Optimal AV delay (AVD) can improve electrical synchrony, and, if adequately timed, may result in fusion pacing. During fusion pacing, the intrinsic conduction wavefront and device pacing are timely fused to produce an enhanced depolarization of the ventricles and increased cardiac output.

Selection between biventricular (BiV) and LV is important. LV only pacing may be more effective than BiV pacing in patients experiencing Left bundle branch block (LBBB). BiV pacing may be more effective tan LV only pacing in patients experiencing Right bundle branch block (RBBB) and reduce cost and procedure time. LV only pacing may avoid the deleterious effects of RV pacing on the LV side of the heart and save battery life for the IMD.

Therefore, a need remains for improved methods and systems for determining whether implement BiV pacing or LV pacing.

SUMMARY

In accordance with embodiments herein, a computer implemented method for detecting arrhythmias in cardiac activity is provided. The method is under control of one or more processors configured with specific executable instructions. The method measures conduction delays between an atria (A) and multiple left ventricular (LV) electrodes to obtain multiple intrinsic A/LV intervals. The method further measures conduction delays between a right ventricular (RV) and the multiple LV electrodes to obtain multiple intrinsic VV intervals. The method calculates g a first atrial ventricular (AV) delay based on at least one of the intrinsic A/LV intervals and calculates a second AV delay based on at least one of the intrinsic VV intervals. The method selects a biventricular (BiV) pacing mode or an LV only pacing mode based on a relation between the first and second AV delays and delivers a pacing therapy based on the selecting operation.

Optionally, the delivering may further comprise delivering the pacing therapy utilizing the first or second AV delay based on a relation between the first and second AV delays. The selecting may further comprise selecting one of the first and second AV delays to be utilized for the pacing therapy based on whether the relation between the first and second AV delays satisfy a criteria. The method may calculate a percentage relation between the first and second AV delays AVD1 and may compare the percentage relation to a criteria. The selecting operation may comprise selecting the BiV pacing mode or the LV only pacing mode based on whether the percentage relation satisfies the criteria. During the LV only pacing mode, the RV may not not paced.

Optionally, the method may comprise measuring a conduction delay between atria and the RV to obtain an intrinsic A/RV interval. The calculating the second AV delay is based on a difference between the intrinsic A/RV interval and a lowest one of the intrinsic W intervals The calculating the second AV delay may further comprise determining a lowest one of the intrinsic VV intervals. The calculating the first AV delay may further comprise determining a lowest one of the intrinsic A/LV intervals. The method may comprise timing delivery of pacing pulses in the BiV pacing mode in a fusion timing manner with intrinsic conduction in at least one of the RV and LV. The method may comprise timing delivery of pacing pulses in the LV only pacing mode in a fusion timing manner with intrinsic conduction from the RV apex along the LV. The measuring the intrinsic VV intervals may further comprise delivering a paced event at each of the LV electrodes and measuring an associated conduction time to an RV electrode.

In accordance with embodiments herein, a system is provided. The system comprises at least one implantable lead comprising an atrial (A) electrode, a right ventricular (RV) electrode and multiple left ventricular (LV) electrodes. The system further comprises at least one processor and a memory. The memory is coupled to the at least one processor. The memory stores program instructions, wherein the program instructions are executable by the at least one processor to measure conduction delays between the A electrode and the LV electrodes to obtain multiple intrinsic A1LV intervals and measures conduction delays between the RV electrode and the LV electrodes to obtain multiple intrinsic VV intervals. They system calculates a first atrial ventricular (AV) delay based on at least one of the intrinsic A/LV intervals and calculates a second AV delay based on at least one of the intrinsic VV intervals. They system selects a biventricular (BiV) pacing mode or an LV only pacing mode based on a relation between the first and second AV delays and delivers a pacing therapy based on the selecting operation.

Optionally, the at least one processor may be further configured to deliver the pacing therapy utilizing the first or second AV delay based on a relation between the first and second AV delays. The at least one processor may be further configured to select one of the first and second AV delays to be utilized for the pacing therapy based on whether the relation between the first and second AV delays satisfy a criteria. The at least one processor may be further configured to calculate a percentage relation between the first and second AV delays AVD1 and may compare the percentage relation to a criteria. The at least one processor may select the BiV pacing mode or the LV only pacing mode based on whether the percentage relation satisfies the criteria. During the LV only pacing mode, the at least one processor may be configured to not pace in the RV.

Optionally, the at least one processor may be further configured to measure a conduction delay between atria and the RV to obtain an intrinsic A/RV interval. The at least one processor may be configured to calculate the second AV delay based on a difference between the intrinsic A/RV interval and a lowest one of the intrinsic W intervals. The at least one processor may be further configured to calculate the second AV delay by determining a lowest one of the intrinsic W intervals. The calculating the first AV delay may further comprises determining a lowest one of the intrinsic A/LV intervals.

Optionally, the at least one processor may be further configured to time delivery of pacing pulses in the BiV pacing mode in a fusion timing manner with intrinsic conduction in at least one of the RV and LV. The at least one processor may be further configured to time delivery of pacing pulses in the LV only pacing mode in a fusion timing manner with intrinsic conduction from the RV apex along the LV. The at least one processor may be further configured to deliver a paced event at each of the LV electrodes and measure an associated conduction time to an RV electrode.

DETAILED DESCRIPTION

The terms "intrinsic A/LV interval" and "intrinsic A/RV interval" are used throughout to refer to measured intrinsic conduction time between a paced or sensed atrial event and an event sensed at a left or right ventricle sensing site, respectively.

The term "PR Interval" collectively refers to intrinsic A/LV intervals and/or intrinsic A/RV intervals.

The terms "atrioventricular delay" and "AVD" are used throughout to refer to a programmed time delay to be used by the implantable medical device in connection with delivering therapy.

The term "LV only pacing" refers to a mode of operation for an implanted medical device in which the LV is paced but the RV is not paced.

In accordance with embodiments herein, methods and systems are described for determining whether to implement biventricular (BiV) or left ventricular (LV) only pacing. Embodiments provide an automated procedure to determine select (e.g., optimal) AVD for effective BiV pacing and/or LV only pacing. The systems and methods adjust an electrical timing for select (e.g., optimal) fusion pacing in a dynamic manner that takes advantage of knowledge of electrical conduction patterns across the RV electrodes and LV electrodes for a particular patient. The fusion pacing may be timed with respect to conduction along the LV or with respect to conduction along the RV apex.

The systems and methods automatically determine an AVD timing in bi-ventricular and LV-only pacing for heart failure patients. The intrinsic A/LV ad A/RB intervals are recorded between the different combinations of sensing sites. The methods and systems make use of the electrical timings (RAs-LVs, RAs-RVs, and LV-RVs) to determine if the BiV pacing and/or LV only pacing may be used.

Figure 1:
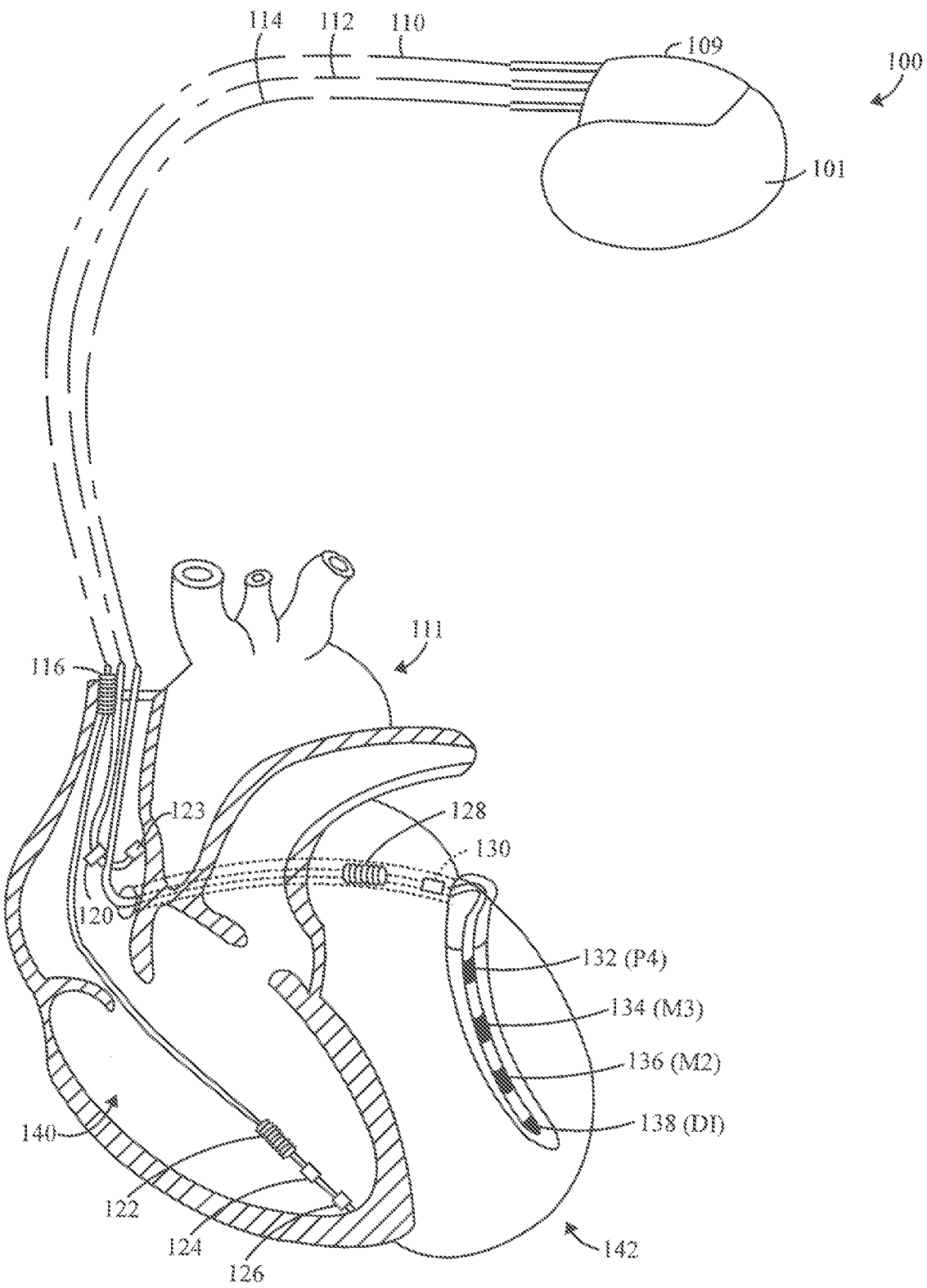
FIG. 1 illustrates an implantable medical device (IMD) Intended for subcutaneous implantation at a site near the heart, in accordance with embodiments herein.

FIG. 1 illustrates an implantable medical device (IMD) 100 intended for subcutaneous implantation at a site near the heart 111, in accordance with embodiments herein. The IMD 100 may be a dual-chamber stimulation device, capable of treating both fast and slow arrhythmias with stimulation therapy, including cardioversion, pacing stimulation, an implantable cardioverter defibrillator, suspend tachycardia detection, tachyarrhythmia therapy, and/or the like. The IMD 100 may include a housing 101 to hold the electronic/computing components. The housing 101 (which is often referred to as the "can," "case," "encasing," or "case electrode") may be programmably selected to act as the return electrode for certain stimulus modes. The housing 101 further includes a connector 109 with a plurality of terminals 200-210 (shown in FIG. 2).

The IMD 100 is shown in electrical connection with a heart 111 by way of a left atrial (LA) lead 120 having a right lead 112 and a left atrial (LA) ring electrode 128. The IMD 100 is also in electrical connection with the heart 111 by way of a right ventricular (RV) lead 110 having, in this embodiment, a left ventricle (LV) electrode 132 (e.g., P4), an LV electrode 134 (e.g., M3), an LV electrode 136 (e.g., M2), and an LV electrode 138 (e.g., D1). The RV lead 110 is transvenously inserted into the heart 111 to place the RV coil 122 in the RV apex, and the SVC coil electrode 116. Accordingly, the RV lead 110 is capable of receiving cardiac signals and delivering stimulation in the form of pacing and shock therapy to the right ventricle 140 (also referred to as the RV chamber). The IMD 100 includes RV electrode 126, and a right atrium (RA) electrode 123. The RV lead 110 includes an RV tip electrode 126, an RV ring electrode 124, an RV coil electrode 122, and an SVC coil electrode 116.

The IMD 100 includes a left ventricle 142 (e.g., left chamber) pacing therapy, and is coupled to a multi-pole LV lead 114 designed for placement in various locations such as a "CS region" (e.g., venous vasculature of the left ventricle, including any portion of the coronary sinus (CS), great cardiac vein, left marginal vein, left posterior ventricular vein, middle cardiac vein, and/or small cardiac vein or any other cardiac vein accessible by the coronary sinus), the epicardial space, and/or the like.

In an embodiment, the LV lead 114 is designed to receive atrial and ventricular cardiac signals and to deliver left ventricular pacing therapy using a set of multiple LV electrodes 132, 134, 136, 138. The LV lead 114 also may deliver left atrial pacing therapy using at least an LA ring electrode 128 and shocking therapy using at least the LA ring electrode 128. In alternate embodiments, the LV lead 114 includes the LV electrodes 138, 136, 134, and 132, but does not include the LA electrode 130. The LV lead 114 may be, for example, the Quartet™ LV pacing lead developed by St. Jude Medical Inc. (headquartered in St. Paul, Minn.), which includes four pacing electrodes on the LV lead. Although three leads 110, 112, and 114 are shown in FIG. 1, fewer or additional leads with various configurations of pacing, sensing, and/or shocking electrodes may optionally be used. For example, the LV lead 114 may have more or less than four LV electrodes 132-138.

When selecting a target venous branch for the LV lead 114, several factors may be taken into account. For example, it may be desirable to maximize the LV mass that may be captured by the LV lead 114. Accordingly, to maximize LV mass exposure, certain venous branches may be preferred for positioning the LV lead 114. Further, a diameter and trajectory of the venous branch are also considered to ensure that the venous branch will support the chronic stability of the LV lead 114. Passive fixation of the LV lead 114 may be established through the anatomy of the host venous branch which causes the LV lead 114 to extend the distal portion thereof in a manner that differs from the LV lead's preformed shape. Optionally, additional factors to be considered when placing the LV lead 114 may include reducing myocardial capture thresholds, avoiding atrial and phrenic nerve stimulation and the like. After the LV lead 114 is positioned, the LV pacing vectors may be selected.

The LV electrode 132 (also referred to as P4) is shown as being the most "distal" LV electrode with reference to how far the electrode is from the right ventricle 140. The LV electrode 138 (also referred to as D1) is shown as being the most "proximal" LV electrode 132-138 to the left ventricle 142. The LV electrodes 136 and 134 are shown as being "middle" LV electrodes (also referred to as M3 and M2), between the distal and proximal LV electrodes 138 and 132, respectively. Accordingly, so as to more aptly describe their relative locations, the LV electrodes 138, 136, 134, and 132 may be referred to respectively as electrodes D1, M2, M3, and P4 (where "D" stands for "distal", "M" stands for "middle", and "P" stands from "proximal", and the s are arranged from most distal to most proximal, as shown in FIG. 1). Optionally, more or fewer LV electrodes may be provided on the lead 114 than the four LV electrodes D1, M2, M3, and P4.

The LV electrodes 132-138 are configured such that each electrode may be utilized to deliver pacing pulses and/or sense pacing pulses (e.g., monitor the response of the LV tissue to a pacing pulse). In a pacing vector or a sensing vector, each LV electrode 132-138 may be controlled to function as a cathode (negative electrode). Pacing pulses may be directionally provided between electrodes to define a pacing vector. In a pacing vector, a generated pulse is applied to the surrounding myocardial tissue through the cathode. The electrodes that define the pacing vectors may be electrodes in the heart 111 or located externally to the heart 111 (e.g., on a housing/case device 101). For example, the housing/case 101 may be referred to as the housing 101 and function as an anode in unipolar pacing and/or sensing vectors. The RV coil 122 may also function as an anode in unipolar pacing and/or sensing vectors. The LV electrodes 132-138 may be used to provide various different vectors. Some of the vectors are intraventricular LV vectors (e.g., vectors between two of the LV electrodes 132-138), while other vectors are interventricular vectors (e.g., vectors between an LV electrode 132-138 and the RV coil 122 or another electrode remote from the left ventricle 142). Below is a list of exemplary bipolar sensing vectors with LV cathodes that may be used for sensing using the LV electrodes D1, M2, M3, and P4 and the RV coil 122. Maybe noted, that various other types of leads and the IMD 100 may be used with various other types of electrodes and combinations of electrodes. The foregoing electrode types/combinations are provided as non-limiting examples. Further, maybe recognized that utilizing an RV coil electrode as an anode is merely one example. Various other electrodes may be configured as the anode electrode.

Figure 2:
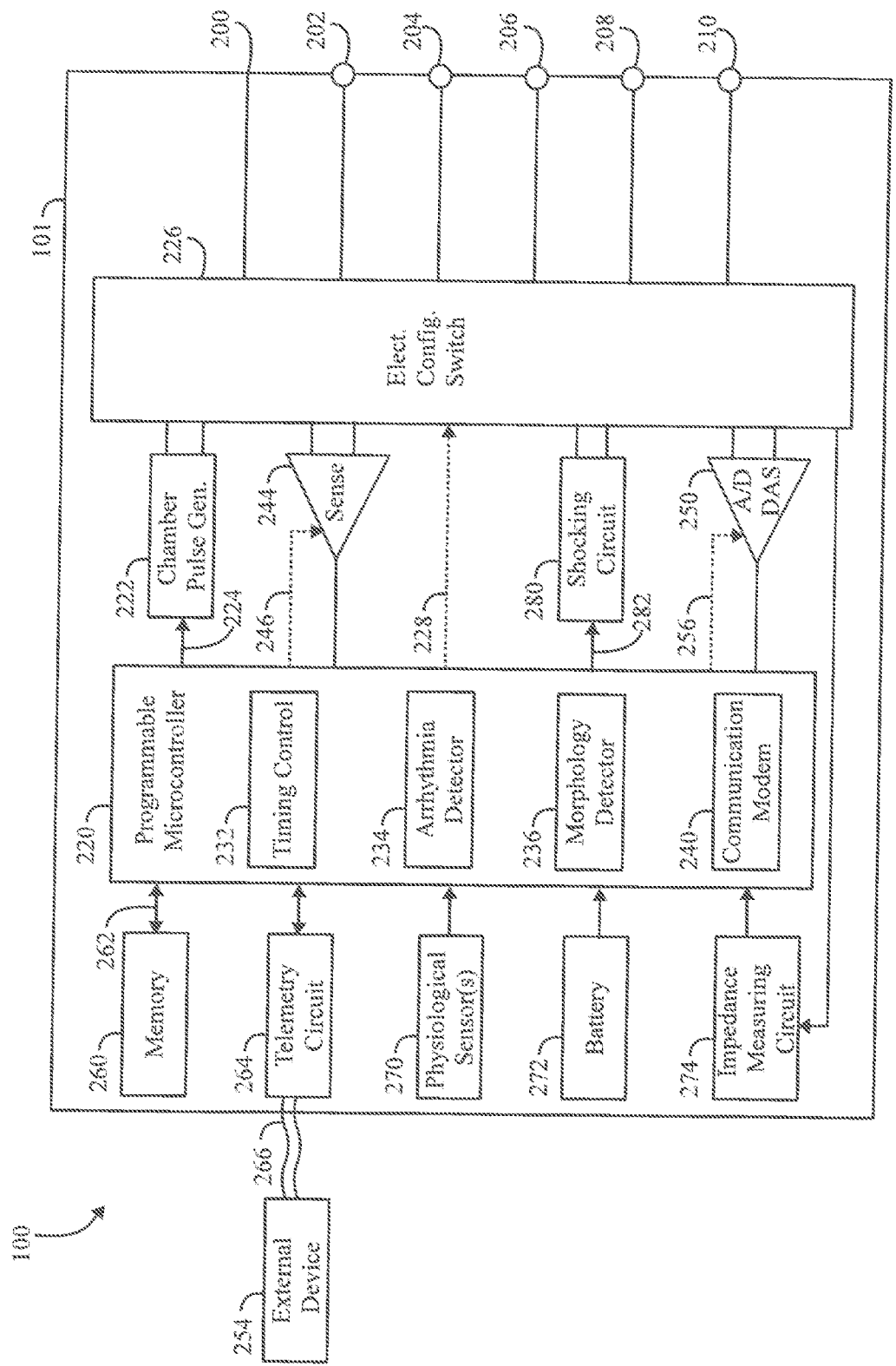
FIG. 2 shows an IMD that is configured to be implanted into the patient as part of an implantable cardiac system, in accordance with embodiments herein.

FIG. 2 illustrates a schematic view of the IMD 100. The IMD 100 may be a dual-chamber stimulation device, capable of treating both fast and slow arrhythmias with stimulation therapy, including cardioversion, pacing stimulation, an implantable cardioverter defibrillator, suspend tachycardia detection, tachyarrhythmia therapy, and/or the like.

The IMD 100 has a housing 101 to hold the electronic/computing components. The housing 101 (which is often referred to as the "can," "case," "encasing," or new to me makes "case electrode") may be programmably selected to act as the return electrode for certain stimulus modes. The housing 101 further includes a connector (not shown) with a plurality of terminals 200-210. The terminals may be connected to electrodes that are located in various locations within and around the heart. For example, the terminals may include: a terminal 200 to be coupled to a first electrode (e.g., a tip electrode) located in a first chamber, a terminal 202 to be coupled to a second electrode located in a second chamber; a terminal 204 to be coupled to an electrode located in the first chamber; a terminal 206 to be coupled to an electrode located in the second chamber; an a terminal 208 to be coupled to an electrode; and a terminal 210 to be coupled to an electrode located in the shocking circuit 280. The type and location of each electrode may vary. For example, the electrodes may include various combinations of a ring, a tip, a coil and shocking electrodes and the like.

The IMD 100 includes a programmable microcontroller 220 that controls various operations of the IMD 100, including cardiac monitoring and stimulation therapy. The microcontroller 220 includes a microprocessor (or equivalent control circuitry), one or more processors, RAM and/or ROM memory, logic and timing circuitry, state machine circuitry, and I/O circuitry. The IMD 100 further includes an atrial and/or ventricular pulse generator 222 that generates stimulation pulses for connecting the desired electrodes to the appropriate I/O circuits, thereby facilitating electrode programmability. The switch 226 is controlled by a control signal 228 from the microcontroller 220.

A pulse generator 222 is illustrated in FIG. 2. Optionally, the IMD 100 may include multiple pulse generators, similar to the pulse generator 222, where each pulse generator is coupled to one or more electrodes and controlled by the microcontroller 220 to deliver select stimulus pulse(s) to the corresponding one or more electrodes. The IMD 100 includes sensing circuitry 244 selectively coupled to one or more electrodes that perform sensing operations, through the switch 226 to detect the presence of cardiac activity in the chamber of the heart 111. The output of the sensing circuitry 244 is connected to the microcontroller 220 which, in turn, triggers, or inhibits the pulse generator 222 in response to the absence or presence of cardiac activity. The sensing circuitry 244 receives a control signal 246 from the microcontroller 220 for purposes of controlling the gain, threshold, polarization charge removal circuitry (not shown), and the timing of any blocking circuitry (not shown) coupled to the inputs of the sensing circuitry.

In the example of FIG. 2, the sensing circuit 244 is illustrated. Optionally, the IMD 100 may include multiple sensing circuits 244, similar to the sensing circuit 244, where each sensing circuit is coupled to one or more electrodes and controlled by the microcontroller 220 to sense electrical activity detected at the corresponding one or more electrodes. The sensing circuit 224 may operate in a unipolar sensing configuration or a bipolar sensing configuration.

The IMD 100 further includes an analog-to-digital (A/D) data acquisition system (DAS) 250 coupled to one or more electrodes via the switch 226 to sample cardiac signals across any pair of desired electrodes. The A/D converter 250 is configured to acquire intracardiac electrogram signals, convert the raw analog data into digital data and store the digital data for later processing and/or telemetric transmission to an external device 254 (e.g., a programmer, local transceiver, or a diagnostic system analyzer). The A/D converter 250 is controlled by a control signal 256 from the microcontroller 220.

The microcontroller 220 includes an arrhythmia detector 234 for analyzing cardiac activity signals sensed by the sensing circuit 244 and/or the A/D converter 250. The arrhythmia detector 234 is configured to analyze cardiac signals sensed at various sensing sites. The arrhythmia detector 234 declares an arrhythmia, in response to which, the microcontroller 220 determines an appropriate therapy. For example, responsive to the arrhythmia detector 234 identifying a bradycardia arrhythmia, the microcontroller 220 directs the pulse generator 222 to deliver a pacing therapy. The microcontroller 220 executes program instructions to implement the operations of FIG. 6, such as to measure conduction delays between the A electrode and the LV electrodes to obtain multiple intrinsic A/LV intervals, measure conduction delays between the RV electrode and the LV electrodes to obtain multiple intrinsic VV intervals, and measure a conduction delay between atria and the RV to obtain an intrinsic A/RV interval. The microcontroller 220 executes program instructions to calculate a first atrial ventricular (AV) delay based on at least one of the intrinsic A/LV intervals and calculate a second AV delay based on at least one of the intrinsic VV intervals. For example, the microcontroller 220 is configured to calculate the second AV delay based on a difference between the intrinsic A/RV interval and a lowest one of the intrinsic VV intervals. The microcontroller 220 is configured to select a biventricular (BiV) pacing mode or an LV only pacing mode based on a relation between the first and second AV delays; and deliver a pacing therapy based on the selecting operation.

Optionally, the microcontroller 220 is further configured to deliver the pacing therapy utilizing the first or second AV delay based on a relation between the first and second AV delays. Optionally, the microcontroller 220 is further configured to select one of the first and second AV delays to be utilized for the pacing therapy based on whether the relation between the first and second AV delays satisfy a criteria. Optionally, the microcontroller 220 is further configured to calculate a percentage relation between the first and second AV delays AVD1 and compare the percentage relation to a criteria. The microcontroller 220 selects the BiV pacing mode or the LV only pacing mode based on whether the percentage relation satisfies the criteria.

During the LV only pacing mode, the microcontroller 220 is configured to not paced in the RV. The microcontroller 220 is further configured to calculate the second AV delay by determining a lowest one of the intrinsic VV intervals. The calculation of the first AV delay further comprises determining a lowest one of the intrinsic A/LV intervals. The microcontroller 220 is further configured to time delivery of pacing pulses in the BiV pacing mode in a fusion timing manner with intrinsic conduction in at least one of the RV and LV. The microcontroller 220 is further configured to time delivery of pacing pulses in the LV only pacing mode in a fusion timing manner with intrinsic conduction from the RV apex along the LV. The microcontroller is further configured to deliver a paced event at each of the LV electrodes and measure an associated conduction time to an RV electrode.

In accordance with embodiments herein, the pacing therapy is BiV pacing or LV only pacing. The BiV pacing or LV only pacing is timed to fuse the pacing pulses with an intrinsic conduction wave front. Among other things, a select (e.g., optimal) pacing threshold is chosen that exhibits no phrenic nerve stimulation (PNS).

Additionally or alternatively, the arrhythmia detector 234 is configured to detect the PNS, which may represent the diaphragm pacing of the rhythmic application of electrical impulses to the diaphragm through the phrenic nerve. For example, the detection of the PNS based on the terminals 200-210 through the switch 226. The microcontroller 220 controls the timing of the stimulation pulses, the timing of refractory periods, blanking intervals, noise detection windows, evoked response windows, alert intervals, marker channel timing, and/or the like.

The microcontroller 220 is operably coupled to a memory 260 by a suitable data/address bus 262. The programmable operating parameters used by the microcontroller 220 are stored in the memory 260 and used to customize the operation of the IMD 100 to suit the needs of a particular patient. The operating parameters of the IMD 100 may be non-invasively programmed into the memory 260 through a telemetry circuit 264 in telemetric communication via communication link 266 (e.g., MICS, Bluetooth low energy, and/or the like) with the external device 254.

The IMD 100 can further include one or more physiological sensors 270. Such sensors are commonly referred to as "rate-responsive" sensors because they are typically used to adjust pacing stimulation rates according to the exercise state of the patient. However, the physiological sensor 156 may further be used to detect changes in cardiac output, changes in the physiological condition of the heart, or diurnal changes in activity (e.g., detecting sleep and wake states). Signals generated by the physiological sensors 270 are passed to the microcontroller 220 for analysis. While shown as being included within the IMD 100, the physiological sensor(s) 270 may be external to the IMD 100, yet still, be implanted within or carried by the patient. Examples of physiological sensors might include sensors that, for example, sense respiration rate, pH of blood, ventricular gradient, activity, position/posture, minute ventilation (MV), and/or the like.

A battery 272 provides operating power to all of the components in the IMD 100. The battery 272 is capable of operating at low current drains for long periods of time, and is capable of providing a high-current pulses (for capacitor charging) when the patient requires a shock pulse (e.g., in excess of 2 A, at voltages above 2 V, for periods of 10 seconds or more). The battery 272 also desirably has a predictable discharge characteristic so that elective replacement time can be detected. As one example, the IMD 100 employs lithium/silver vanadium oxide batteries.

The IMD 100 further includes an impedance measuring circuit 274, which can be used for many things, including sensing respiration phase. The impedance measuring circuit 274 is coupled to the switch 226 so that any desired electrode and/or terminal may be used to measure impedance in connection with monitoring respiration phase.

The microcontroller 220 further controls a shocking circuit 280 by way of a control signal 282. The shocking circuit 280 generates shocking pulses of low (e.g., up to 0.5 joules), moderate (e.g., 0.5-10 joules), or high energy (e.g., 11 to 40 joules), as controlled by the microcontroller 220. Such shocking pulses are applied to the patient's heart through shocking electrodes. Maybe noted that the shock therapy circuitry is optional and may not be implemented in the IMD 100.

The microcontroller 220 further includes timing control 232 used to control the timing of such stimulation pulses (e.g., pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and the like. The switch 226 includes a plurality of switches for connecting the desired electrodes to the appropriate I/O circuits, thereby providing complete electrode programmability. Accordingly, the switch 226, in response to a control signal 228 from the microcontroller 220, determines the polarity of the stimulation pulses (e.g., unipolar, bipolar, etc.) by selectively closing the appropriate combination of switches (not shown) as is known in the art.

The microcontroller 220 is illustrated to include timing control 232 to control the timing of the stimulation pulses (e.g., pacing rate, atrioventricular (AV) delay, atrial interconduction (A-A) delay, or ventricular interconduction (V-V) delay, etc.). The AV delay is managed to provide a fusion AV delay to fuse timing of pacing pulses with intrinsic wave fronts. The timing control 232 may also be used for the timing of refractory periods, blanking intervals, noise detection windows, evoked response windows, alert intervals, marker channel timing, and so on. Microcontroller 220 also has a morphology detector 236 to review and analyze one or more features of the morphology of cardiac signals. Although not shown, the microcontroller 220 may further include other dedicated circuitry and/or firmware/software components that assist in monitoring various conditions of the patient's heart and managing pacing therapies.

The IMD 100 is further equipped with a communication modem (modulator/demodulator) 240 to enable wireless communication with other devices, implanted devices and/or external devices. In one implementation, the communication modem 240 may use high-frequency modulation of a signal transmitted between a pair of electrodes. As one example, the signals may be transmitted in a high-frequency range of approximately 10-80 kHz, as such signals travel through the body tissue and fluids without stimulating the heart or being felt by the patient.

Figure 3:
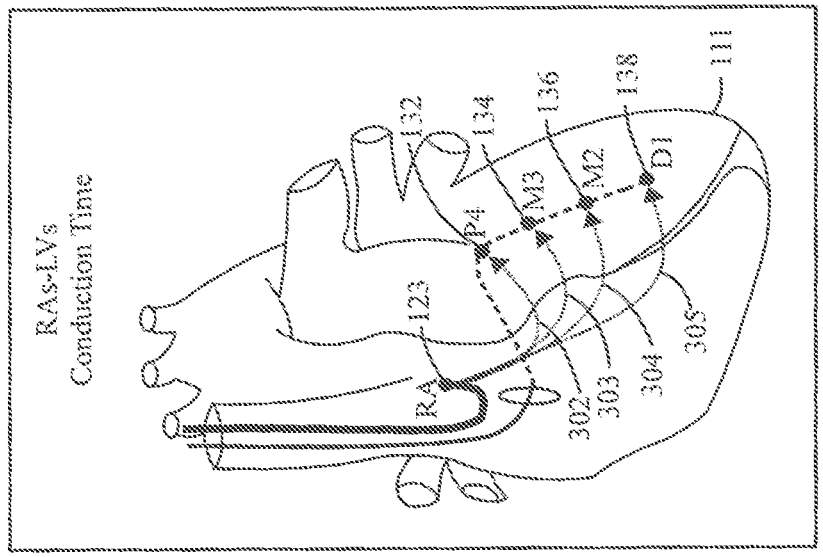
FIG. 3 illustrates an atrioventricular delay between a right atrium electrode and a left ventricular paced electrode, in accordance with embodiments herein.

FIG. 3 illustrates intrinsic A/LV intervals between an RA electrode 123 and the LV electrodes 132-138, measured in accordance with embodiments herein. For example, the microcontroller 220 may measure the conduction time for an event propagation between the RA electrode 123 and each of the LV electrodes 132-138. The microcontroller 220 may initiate a paced event at the RA electrode 123, or may sense an intrinsic event at the RA electrode 123. The microcontroller 220 measures conduction time (e.g., the conduction time) for a conduction wave to propagate between the pacing/sensed event at the RA electrode 123 to a sensed event at each of the LV electrodes 132-138. The microcontroller 220 may compare the amount of time received at the LV electrodes 132-138. The microcontroller 220 identifies the conduction time received by the LV electrodes 132-138 relative to each other, to identify the lowest conduction time (lowest intrinsic A/LV interval 302-305) relative to the LV electrodes 132-138.

Figure 4:
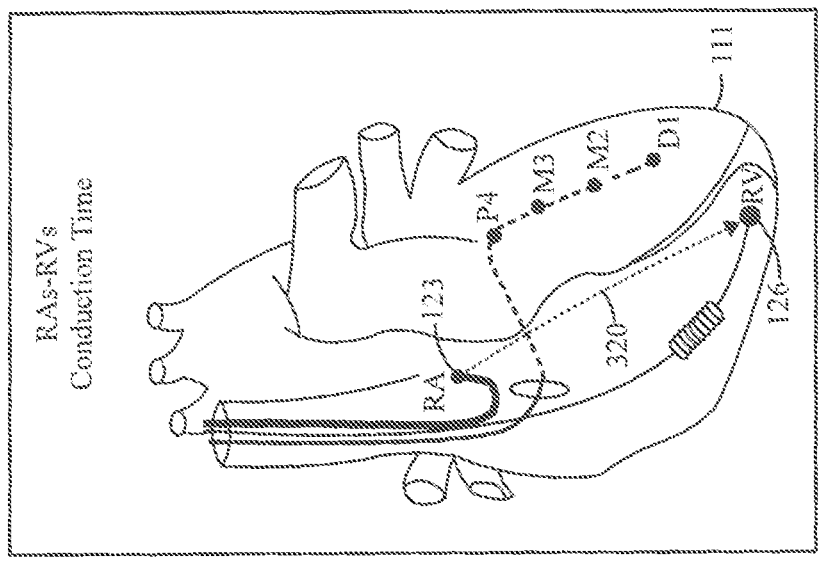
FIG. 4 illustrates a PR interval between a right atrium electrode and a right ventricular electrode, in accordance with embodiments herein.

FIG. 4 illustrates an intrinsic A/RV interval between the RA electrode 123 and the RV electrode 126, measured in accordance with embodiments herein. For example, the microcontroller may measure the conduction time between the RA electrode 123 and the RV electrode 126. The microcontroller 220 may initiate a pacing event at the RA electrode 123 using the switch 226. The microcontroller 220 then measures the amount of time (e.g., the intrinsic A/RV interval 320) between the paced event at the RA electrode 123 to the sensed event at the RV electrode 126.

Figure 5:
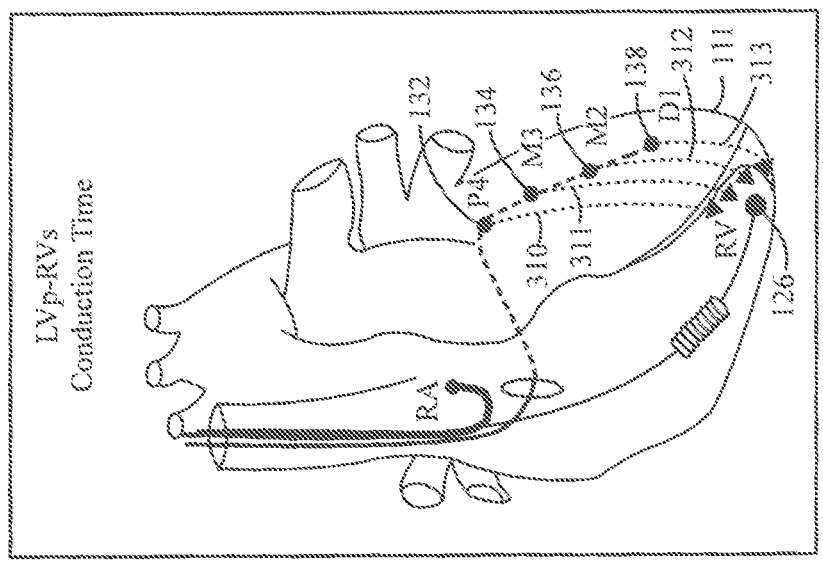
FIG. 5 illustrates an atrioventricular delay between and a left ventricular paced electrode and a right ventricular electrode, in accordance with embodiments herein.

FIG. 5 illustrates intrinsic inter-ventricular interval between each of the LV electrodes 132-138 and the RV electrode 126, measured in accordance with embodiments herein. For example, the microcontroller 220 may measure the intrinsic conduction time between the RV electrode 126 and a select one of the LV electrodes 132-138 by initiating a paced event at the select one of the LC electrodes 132-138 and measuring an amount of time until sensing the event at the RV electrode 126. For example, the microcontroller 220 repeats the pacing operation to measure the amount of time (e.g., intrinsic interventricular interval) for each of the LV electrodes 132-138. In FIG. 5, example intrinsic interventricular (VV) intervals 310-313 are illustrated. The microcontroller 220 compares the intrinsic VV intervals for the LV electrodes 132-138 relative to each other, to identify the lowest intrinsic W interval for an associated one of the LV electrodes 132-138.

The methods and systems herein utilize the measured intrinsic A/LV, VV and A/RV intervals to automatically determine whether to utilize BiV pacing or LV pacing and the AVD to use there with to achieve fusion timing.

Figure 6:
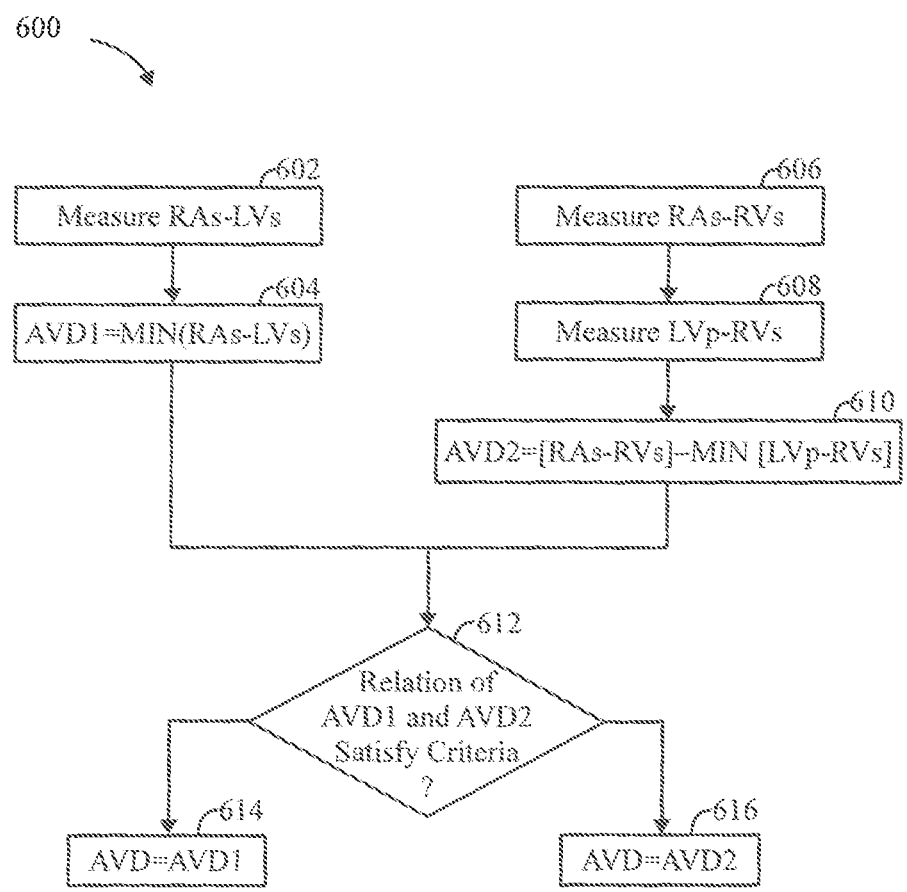
FIG. 6 illustrates a computer implemented process for discriminating between biventricular (BiV pacing) and left ventricular (LV pacing), in accordance with embodiments herein.

FIG. 6 illustrates a computer implemented method 600 for discriminating between biventricular (BiV) pacing and left ventricular (LV) only pacing, in accordance with embodiments herein. The method 600 may be under control of one or more processors configured with specific executable instructions.

At 602, the one or more processors measure an intrinsic A/LV interval for each of the LV sensing sites. For example, in connection with FIG. 3, the one or more processors measure the conduction time between the RA electrode 123 and each of the LV electrodes 132-138. The one or more processors may utilize a sensed event or paced event at the RA electrode 123 to start one or more timers. The timers identify the conduction time at which a propagating wave progresses across the LV until sensed by the LV electrodes 132-138. The one or more processors compare the conduction times for the intrinsic AV intervals at the LV electrode 132-138 relative to each other to identify the intrinsic AV interval that has a desired characteristic (e.g., the minimum intrinsic AV interval).

At 604, the one or more processors defines a first AV delay (AVD1) between the RA and the LV. For example, the one or more processors identify the lowest conduction time between the RA electrode 123 and one of the LV electrodes 132-138. The one or more processors compare the conduction times for the intrinsic A/LV intervals measured at the LV electrode 132-138 relative to each other to identify the intrinsic A/LV interval that has a desired characteristic (e.g., the minimum intrinsic AV interval). The one or more processors sets the intrinsic A/LV interval that has the lowest conduction time as the AVD1.

At 606, the one or more processors measure a conduction time (e.g., an intrinsic A/RV interval) between the RA and the RV. For example, in connection with FIG. 4, the one or more processors measure the conduction time between the RA electrode 123 and the RV electrode 126. The one or more processors initiate a timer when detecting an intrinsic event or when a paced event occurs at the RA. The timer is stopped when the propagating wave is sensed at an RV site such as the RV electrode 126. The one or more processors identify the intrinsic A/RV interval based on the timer.

At 608, the one or more processors measure an intrinsic W interval between each of the LV sensing sites and an RV sensing site. For example, in connection with FIG. 5, the one or more processors measure the conduction time between each of the LV electrodes 132-138 and the RV electrode 126. For example, the one or more processors direct the IMD to deliver a paced event at a first LV electrode (e.g., P4, 132) and then measures the conduction time until a corresponding propagation wave reaches the RV sensing site (e.g., 126). Next, the one or more processors direct the IMD to deliver a paced event at a second LV electrode (e.g., M3, 134) and then measures the conduction times until a corresponding propagation wave reaches the RV sensing site (e.g., 126). Next, the one or more processors direct the IMD to deliver a paced event at a third LV electrode (e.g., M2, 136) and then measures the conduction time until a corresponding propagation wave reaches the RV sensing site (e.g., 126). Next, the one or more processors direct the IMD to deliver a paced event at a fourth LV electrode (e.g., D1, 138) and then measures the conduction time until a corresponding propagation wave reaches the RV sensing site (e.g., 126). The one or more processors identify the conduction times associated with the LV electrodes 132-138, relative to each other, to identify the lowest intrinsic VV interval 310-313 relative from an LV electrode 132-138 to the RV.

At 604, the one or more processors defines a first AV delay (AVD1) between the RA and the LV. For example, the one or more processors identify the lowest conduction time between the RA electrode 123 and one of the LV electrodes 132-138. The one or more processors compare the conduction times for the intrinsic A/LV intervals measured at the LV electrode 132-138 relative to each other to identify the intrinsic AILV interval that has a desired characteristic (e.g., the minimum intrinsic AV interval). The one or more processors sets the intrinsic A/LV interval that has the lowest conduction time as the AVD1.

At 610, the one or more processors define a second AV delay (AVD2). The one or more processors determine the AVD2 based on the intrinsic A/RV and VV intervals. For example, the one or more processors identify the lowest intrinsic VV interval between the LV electrodes 132-138 and the RV electrode. The processors subtract the lowest VV intrinsic VV interval from the intrinsic A/RV interval to obtain the second AV delay AVD2.

At 612, the one or more processors determine whether a relation between the first and second AV delays (AVD1 and AVD2) satisfies a criteria (e.g. within a percentage of one another). For example, the criteria may represent requirement that the first AV delay is within a percentage threshold of the second AV delay under 100% (e.g., the AVD1 is 90%, 80%, 70% of the AVD2). The relation between the AVD1 and AVD2 may indicate conduction block on the right side or left side of the heart 111. For example, when AVD1 and AVD2 are within the relation of one another, the one or more processors may identify a RBBB condition. When an RBBB condition exists, BiV pacing is preferred to synchronize RV and LV conduction and contraction.

Alternatively, when the relation of the AVD1 and AVD2 is outside of the criteria, the condition represents slower conduction on the left side of the heart 111 as compared to the right side. Accordingly, the one or more processors identify an LBBB condition, in which case LV only pacing is desired because the RV is exhibiting normal conduction and doesn't need to be paced. By limiting pacing to LV only pacing, battery life is preserved and extended.

At 614, the one or more processors initiate BiV pacing at the RV electrode 126 and one or more of the LV electrodes 132-138. The one or more processors set the AV delay for BiV pacing based on the first AV delay (AVD1) which corresponds to the minimum intrinsic A/LV interval. The one or more processors is configured to provide BiV pacing with paced events timed/fused to a select LV site to match the intrinsic conduction of the heart 111. The one or more processors match the pacing timing to the intrinsic conduction to form fusion during the BiV pacing.

At 616, the one or more processors initiate LV only pacing of one or more LV electrodes 132-138 and do not pace the RV. The one or more processors set the AV delay for LV only pacing based on the intrinsic A/RV interval and the intrinsic VV interval. The one or more processors is configured to provide LV only pacing with paced events timed/fused to activation at the RV apex (proximate the RV tip electrode 126) to match the intrinsic conduction of the heart 111 when propagating from the RV apex. The one or more processors match the pacing to form fusion with the LV electrodes 132-138.

Optionally, the LV pacing side maybe selected in various manners. For example, the LV pacing site may be set to correspond to the LV sensing site that exhibited the latest conduction time (e.g., longest intrinsic A/LV interval or longest intrinsic VV interval)

CLOSING

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A system, the system comprising:
   at least one implantable lead comprising an atrial (A) electrode, a right ventricular (RV) electrode and multiple left ventricular (LV) electrodes;
   at least one processor; and
   a memory coupled to the at least one processor, wherein the memory stores program instructions, wherein the program instructions are executable by the at least one processor to:
   measure conduction delays between the A electrode and two or more of the LV electrodes to obtain multiple corresponding intrinsic A/LV intervals;
   measure conduction delays between the RV electrode and two or more of the LV electrodes to obtain multiple corresponding intrinsic VV intervals;
   calculate a first atrial ventricular (AV) delay based on at least one of the intrinsic A/LV intervals;
   calculate a second AV delay based on at least one of the intrinsic VV intervals;
   select between i) a biventricular (BiV) pacing mode and ii) an LV only pacing mode based on a relation between the first and second AV delays; and
   deliver a pacing therapy based on the selecting operation.

2. The system of claim 1, wherein the at least one processor is further configured to deliver the pacing therapy utilizing the first or second AV delay based on whether the relation between the first and second AV delays indicates conduction block on a right or left side of the heart.

3. The system of claim 1, wherein the at least one processor is further configured to select one of the first and second AV delays to be utilized for the pacing therapy based on whether the relation between the first and second AV delays satisfy a criteria.

4. The system of claim 1, wherein the at least one processor is further configured to calculate a percentage relation between the first and second AV delays and compare the percentage relation to a criteria, the at least one processor to select between the BiV pacing mode and the LV only pacing mode based on whether the percentage relation satisfies the criteria.

5. The system of claim 1, wherein, during the LV only pacing mode, the at least one processor is configured to not pace in the RV.

6. The system of claim 1, wherein the at least one processor is further configured to measure a conduction delay between atria and the RV to obtain an intrinsic A/RV interval, wherein the at least one processor is configured to calculate the second AV delay based on a difference between the intrinsic A/RV interval and a lowest one of the intrinsic VV intervals.

7. The system of claim 1, wherein the at least one processor is further configured to calculate the second AV delay by determining a lowest one of the intrinsic VV intervals; and wherein the calculating the first AV delay further comprises determining a lowest one of the intrinsic A/LV intervals.

8. The system of claim 1, wherein the at least one processor is further configured to time delivery of pacing pulses in the BiV pacing mode in a fusion timing manner with intrinsic conduction in at least one of the RV and LV.

9. The system of claim 1, wherein the at least one processor is further configured to time delivery of pacing pulses in the LV only pacing mode in a fusion timing manner with intrinsic conduction from the RV apex along the LV.

10. The system of claim 1, wherein the at least one processor is further configured to deliver a paced event at each of the LV electrodes and measure an associated conduction time to an RV electrode.

11. The system of claim 1, wherein the at least one processor is further configured to select between i) the BiV pacing mode and ii) the LV only pacing mode based on whether the relation between the first and second AV delays indicates conduction block on a right or left side of the heart.

12. A system, the system comprising:
   at least one implantable lead comprising an atrial (A) electrode, a right ventricular (RV) electrode and multiple left ventricular (LV) electrodes;
   at least one processor; and
   a memory coupled to the at least one processor, wherein the memory stores program instructions, wherein the program instructions are executable by the at least one processor to:
   measure a conduction delay between the A electrode and an LV electrode to obtain an intrinsic A/LV interval;
   measure a conduction delay between the RV electrode and the LV electrode to obtain an intrinsic VV interval;
   calculate first and second atrial ventricular (AV) delays based on the intrinsic A/LV interval and the intrinsic VV interval;
   determine whether a relation between the first and second AV delays indicates conduction block on a right side or a left side of the heart;
   select between i) a biventricular (BiV) pacing mode and ii) an LV only pacing mode based on whether the relation indicates conduction block on the right side or the left side of the heart; and
   deliver a pacing therapy based on the selecting operation.

13. The system of claim 12, wherein the at least one processor is further configured to deliver the pacing therapy utilizing the first or second AV delay based on whether the relation between the first and second AV delays indicates conduction block on the right or left side of the heart.

14. The system of claim 12, wherein the at least one processor is further configured to calculate a percentage relation between the first and second AV delays and compare the percentage relation to a criteria, the at least one processor to select between the BiV pacing mode and the LV only pacing mode based on whether the percentage relation satisfies the criteria.

15. The system of claim 12, wherein the at least one processor is further configured to measure a conduction delay between atria and the RV to obtain an intrinsic A/RV interval, wherein the at least one processor is configured to calculate the second AV delay based on a difference between the intrinsic A/RV interval and a lowest one of the intrinsic VV intervals.

16. The system of claim 12, wherein the at least one processor is further configured to calculate the second AV delay by determining a lowest one of the intrinsic VV intervals; and wherein the calculating the first AV delay further comprises determining a lowest one of the intrinsic A/LV intervals.

17. The system of claim 12, wherein the at least one processor is further configured to time delivery of pacing pulses in the BiV pacing mode in a fusion timing manner with intrinsic conduction in at least one of the RV and LV.

18. The system of claim 12, wherein the at least one processor is further configured to time delivery of pacing pulses in the LV only pacing mode in a fusion timing manner with intrinsic conduction from the RV apex along the LV.

19. The system of claim 12, wherein the at least one processor is further configured to deliver a paced event at each of the LV electrodes and measure an associated conduction time to an RV electrode.

20. The system of claim 12, wherein the at least one processor is further configured to select between i) the BiV pacing mode and ii) the LV only pacing mode based on whether the relation between the first and second AV delays indicates conduction block on a right or left side of the heart.

\* \* \* \* \*